United States Patent
Matar

(10) Patent No.: US 8,790,322 B2
(45) Date of Patent: Jul. 29, 2014

(54) STOMA COAT

(75) Inventor: Nedal Matar, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 13/812,733

(22) PCT Filed: Aug. 3, 2010

(86) PCT No.: PCT/EP2010/004759
§ 371 (c)(1),
(2), (4) Date: Apr. 8, 2013

(87) PCT Pub. No.: WO2012/016575
PCT Pub. Date: Feb. 9, 2012

(65) Prior Publication Data
US 2013/0204216 A1    Aug. 8, 2013

(51) Int. Cl.
*A61F 5/44*    (2006.01)
(52) U.S. Cl.
USPC ............................ 604/332; 604/337; 604/338
(58) Field of Classification Search
USPC .......................................... 604/337, 338, 332
See application file for complete search history.

(56) References Cited

U.S. PATENT DOCUMENTS

| | | | |
|---|---|---|---|
| 4,183,357 A | 1/1980 | Bentley et al. | |
| 4,245,652 A * | 1/1981 | Kelly et al. | 600/549 |
| 4,381,765 A * | 5/1983 | Burton | 600/32 |
| 4,534,761 A | 8/1985 | Raible | |
| 4,555,242 A | 11/1985 | Saudagar | |
| 5,269,774 A * | 12/1993 | Gray | 604/343 |
| 5,356,432 A * | 10/1994 | Rutkow et al. | 623/23.72 |
| 6,669,735 B1 * | 12/2003 | Pelissier | 623/23.74 |
| 8,288,586 B2 * | 10/2012 | Cheon et al. | 562/490 |
| 8,449,512 B2 * | 5/2013 | Villani et al. | 604/332 |
| 2008/0269698 A1 * | 10/2008 | Alexander et al. | 604/332 |
| 2009/0299388 A1 * | 12/2009 | Barker et al. | 606/155 |
| 2011/0015475 A1 * | 1/2011 | Hanuka et al. | 600/32 |
| 2011/0092929 A1 * | 4/2011 | Weig | 604/338 |

FOREIGN PATENT DOCUMENTS

WO    WO 94/15558 A1    7/1994
WO    WO 99/43277 A1    9/1999

* cited by examiner

*Primary Examiner* — Tatyana Zalukaeva
*Assistant Examiner* — Ginger T Chapman
(74) *Attorney, Agent, or Firm* — Saliwanchik, Lloyd & Eisenschenk

(57) ABSTRACT

The present invention relates to a prosthesis, referred to as stoma coat, for implantation in a body wall for cooperating with a body duct to provide a stoma, as well as to its use in a surgical method for creating a stoma. The present invention further relates to accessories for use with said prosthesis and to a kit comprising said prosthesis and said accessories.

32 Claims, 10 Drawing Sheets

STOMA COAT

CROSS REFERENCE TO A RELATED APPLICATION

This application is a National Stage Application of International Application Number PCT/EP2010/004759, filed Aug. 3, 2010; which is incorporated herein by reference in its entirety.

The present invention relates to a prosthesis, referred to as stoma coat, for implantation in a body wall for cooperating with a body duct to provide a stoma, as well as to its use in a surgical method for creating a stoma. The present invention further relates to accessories for use with said prosthesis and to a kit comprising said prosthesis and said accessories.

A stoma (pl. stomata) is a surgically created (artificial) opening in the body, which connects a portion of the body cavity to the outside environment to provide a conduit for allowing elimination of waste material from the patient's body. Surgical procedures in which stomata are created are ended in the suffix "-ostomy" and begin with a prefix denoting the organ or area being operated on. For example, a colostomy involves the large bowel (colon), an ileostomy involves the terminal part of small bowel (ileum) and a urostomy involves the urinary tract.

Stomata to collect feces connect to the bowel (intestine), stomata to collect urine connect to the ureter (the tube that carries urine from the kidneys to the bladder). The waste products are collected in a reservoir bag, or pouch, appended to the patient's body.

A stoma can be either temporary or permanent, depending on the type of operation and how much of the bowel or urinary tract has been removed. The size and shape of the stoma will also depend on the type of operation. Usually, a stoma is a bud-like structure that is formed when the surgeon stitches the opening of the bowel or ureter to the skin of the abdomen, which represents the traditional method of creating a stoma.

One way of appending a collecting bag to a patient's body is by means of an adhesive and gummy sealant about the stoma to hold and seal the device to the skin of the patient. Such materials have been found to cause irritation of the skin about the stoma. So called "contact dermatitis" can further be caused by direct contact between waste materials (i.e. feces or urine) and the skin, and may develop into an infectious dermatitis.

Additionally, stomata are often subject to postoperative problems, some of which can become serious enough to require postoperative treatment or further surgery.

For example, colostomy stomata are sometimes subject to postoperative herniation. A weak spot in the abdominal wall may occur at the point where the colon passes into the abdominal wall. Herniation may occur by the small or large intestine being forced into the abdominal wall at that weak spot.

Another problem which may be experienced is postoperative prolapse of the colon or ileum. This can occur when intraabdominal pressure forces the colon or ileum to literally turn inside out and to protrude in such a manner as to prolapse internal sections of the colon or ileum through the opening in the body wall.

A further potential problem is serositis (inflammation of the serosa of the colon or ileum), due to exposure of the body duct to air, which is particularly acute in stomata which are formed by the traditional method of suturing the colon or ileum directly to the skin surrounding the opening in the abdominal wall.

Other problems include ischemic necrosis, strangulation, stenosis, obstruction and stomal bowel retraction.

It was an object of the present invention to provide an appliance for a stoma that prevents some and preferably all of the above problems. It was also an object of the present invention to provide an appliance which is reliable, secure and as comfortable as possible for the patient. Furthermore, its manufacturing should not be expensive.

The objects of the present invention are solved by a stoma coat, comprising
 a flexible cone-shaped sleeve of a first biocompatible material having a narrow end and a wider end opposite of said narrow end, and further having an external flange and an internal flange located at said narrow end and
 a rigid tube of a second biocompatible material having an outside diameter, a distal end and a proximal end opposite of said distal end, and further having a smooth inner surface and a threaded outer surface, wherein said proximal end is connected with said narrow end of said cone-shaped flexible sleeve.

Said rigid tube has a cylindrical shape and forms the distal part, and said flexible cone-shaped sleeve forms the proximal part of said stoma coat. When said stoma coat is implanted in a body wall for cooperating with a body duct to provide a stoma as envisioned by the present invention, said proximal part, which is also referred to as body of said stoma coat, is located within the peritoneal cavity (intraperitoneal), whereas said distal part is located within the body wall, i.e. within the abdominal wall (between peritoneum and skin), and outside the body, i.e. outside the skin of the abdominal wall (extracutaneous or extraabdominal). Said rigid tube can then further be divided into a neck (region) located within the body wall and a head (region) located outside the body. Said external flange and said internal flange located at said narrow (apical) end of said flexible cone-shaped sleeve can be regarded as forming the border between said distal part and said proximal part, with the distal surface of the external flange being in contact with the inner face of said body wall, i.e. the peritoneum. Whereas said internal flange protrudes inward, i.e. into the cavity of said flexible cone-shaped sleeve, said external flange protrudes outward, i.e. away from said flexible cone-shaped sleeve. Preferably, said internal flange and said external flange are aligned. The stoma coat according to the present invention has a distal opening at the distal end (head) of the rigid tube and a proximal opening at the wider end of the flexible cone-shaped sleeve, where the body duct enters the stoma coat. Said distal opening of the stoma coat allows to drain waste material from the body duct (see, for example, FIGS. 1 and 4).

In one embodiment, said external flange and said internal flange are made of said first biocompatible material.

Preferably, said first biocompatible material is a soft and flexible material, which allows to reverse said flexible cone-shaped sleeve by hand, wherein the wider end of the flexible cone-shaped sleeve is moved towards the distal end of the rigid tube. Reversing said flexible cone-shaped sleeve exposes said internal flange allowing end-to-end anastomosis between said internal flange and the end of the body duct (see, for example, FIGS. 2 and 3).

In one embodiment, said first biocompatible material is selected from the group comprising plastics and silicones, preferably silicone rubber. Preferably, said silicone(s) are implantable medical grade silicones.

In one embodiment, said flexible cone-shaped sleeve has a length of about 8 to 15 cm, preferably of about 12 to 15 cm. Preferably, the diameter of said wider end and the diameter of said narrow end of said flexible cone-shaped sleeve are adjusted to the patient (e.g. in terms of size or age) as well as to the body duct to be stomatized (e.g. colon, ileum or ureter). The diameter of said narrow end of said flexible cone-shaped sleeve matches said outside diameter of said rigid tube.

In one embodiment, said second biocompatible material is a polyolefin, preferably selected from the group comprising polypropylene (PP), polyethylene (PE), as well as copolymers thereof.

In one embodiment, said rigid tube has a length of about 5 to 15 cm, preferably of about 10 to 15 cm. Preferably, said outside diameter (and an internal diameter or a wall thickness) of said rigid tube are adjusted to the patient (e.g. in terms of size or age) as well as to the body duct to be stomatized (e.g. colon, ileum or ureter).

In one embodiment, said flexible cone-shaped sleeve has an inner surface and an outer surface, wherein only said inner surface is coated with a mesh (forming a mesh layer) promoting in-growth of animal tissue, preferably human tissue (e.g. the serosa), and thus adhesion between said inner surface of said flexible cone-shaped sleeve and the body duct. Reversing said flexible cone-shaped sleeve exposes said inner surface (see, for example, FIGS. 2 and 3). Said outer surface is smooth and does not allow reactions with or adhesion to surrounding body parts/bowels.

Preferably, said mesh or mesh layer promoting in-growth of animal tissue, preferably human tissue, is made of a biocompatible non-absorbable material, preferably selected from the group comprising polypropylene (PP) and expanded polytetrafluorethylene (e-PTFE). The mesh layer should be thick enough in order to allow secure attachment and adhesion with the body duct; preferably, said mesh layer has a diameter of at least 0.4 mm.

Preferably, said external flange is part of said outer surface of said flexible cone-shaped sleeve, and said internal flange is part of said inner surface of said flexible cone-shaped sleeve, said inner surface being coated with said mesh. Accordingly, said internal flange is completely coated with said mesh.

In one embodiment, said external flange has a distal surface and a proximal surface, wherein only said distal surface is coated with a mesh promoting in-growth of animal tissue, preferably human tissue, as defined above, and wherein said proximal surface is smooth.

Preferably, said external flange protrudes about 2 to 5 cm, preferably about 3 to 4 cm from said flexible cone-shaped sleeve. Preferably, said internal flange protrudes about 0.5 to 1.5 cm, preferably about 1 cm from said flexible cone-shaped sleeve.

In one embodiment, said stoma coat further comprises a first circular flat washer having a circular opening with a diameter matching said outside diameter of said rigid tube, wherein said first circular flat washer is a threaded washer and is screwed onto said rigid tube.

In one embodiment, said first circular flat washer is made of a relatively rigid, but slightly flexible biocompatible, non-absorbable material, preferably selected from the group comprising nylon and polypropylene (PP), in particular prolene.

In one embodiment, said first circular flat washer has a distal surface and a proximal surface, wherein only said proximal surface is coated with a mesh promoting in-growth of animal tissue, preferably human tissue, and wherein said distal surface is smooth, i.e. non-reactive with and non-adhesive to surrounding body parts/organs.

In a preferred embodiment, said first circular flat washer is also referred to as fascia washer, since the implanted stoma coat can be fixated in its position by screwing the first circular flat washer onto the rigid tube starting at the distal end of the rigid tube until said proximal surface of said first washer is in contact with the anterior fascia of the abdominal muscles (e.g. Musculus rectus abdominis) and connecting said washer with the anterior fascia.

Preferably, said first circular flat washer protrudes about 3 to 5 cm from said rigid tube, when screwed onto said rigid tube, i.e. the overall diameter of said first circular flat washer equals the sum of said outside diameter of said rigid tube and 2×3 to 5 cm.

In one embodiment, said stoma coat further comprises a second circular flat washer having a circular opening with a diameter matching said outside diameter of said rigid tube, wherein said second circular flat washer is a threaded washer and is screwed onto said rigid tube, wherein said second circular flat washer is closer to said distal end of said rigid tube than said first circular flat washer.

In one embodiment, said second circular flat washer is made of a relatively rigid, but slightly flexible biocompatible, non-absorbable material, preferably selected from the group comprising nylon and polypropylene (PP), in particular prolene.

In one embodiment, said second circular flat washer has a distal surface and a proximal surface, wherein both surfaces are smooth, i.e. non-reactive with and non-adhesive to surrounding body parts/skin.

In one embodiment, said second circular flat washer comprises an isolation ring made of rubber or any other isolating material, wherein, preferably, said isolation ring is adjacent to the inner ring of said second circular flat washer and seals the contact zone between the abdominal skin and the head of the stoma coat protruding from the abdominal skin.

Said second circular flat washer is also referred to as skin washer, since the implanted stoma coat can be further fixated in its position by screwing the second circular flat washer onto the rigid tube until the proximal surface of said second washer is in contact with the skin of said body wall, preferably the abdominal skin.

Preferably, said second circular flat washer protrudes about 2.5 to 3.5 cm, preferably about 3 cm from said rigid tube, when screwed onto said rigid tube, i.e. the overall diameter of said first circular flat washer equals the sum of said outside diameter of said rigid tube and 2× about 2.5 to 3.5 cm, preferably 2× about 3 cm.

The objects of the present invention are also solved by a stoma coat as defined above for use in a surgical method of making a stoma in a body wall of the animal body, preferably of the human body.

The objects of the present invention are also solved by a circular flat washer for use with a stoma coat as defined above, wherein said circular flat washer is a threaded washer having a circular opening with a diameter matching said outside diameter of said rigid tube of said stoma coat.

In one embodiment, one side of said circular flat washer is coated with a mesh promoting in-growth of animal tissue, preferably human tissue.

Preferably, said circular flat washer has an overall diameter which equals the sum of said outside diameter of said rigid tube and 2×2.5 to 5 cm.

The objects of the present invention are also solved by a collecting bag, as shown in FIG. 7, for use with a stoma coat as defined above, wherein said collecting bag 21 comprises an opening 22 with a circular threaded linking piece 23 having an inside diameter matching said outside diameter of said rigid tube of said stoma coat, and wherein said collecting bag is screwed onto said distal end of said rigid tube, i.e. the head (region) of said rigid tube.

Preferably, said collecting bag is a disposable bag, made of one or more inexpensive, liquid impermeable materials, such as plastic (e.g. PE, PP, nylon), rubber and silicone.

The objects of the present invention are also solved by a cap as shown in FIG. 8, for use with a stoma coat as defined above, wherein said cap 24 is a threaded cap having an inside diameter matching said outside diameter of said rigid tube of said stoma coat, and wherein said cap is screwed onto said distal end (head) of said rigid tube.

Preferably, said cap is a disposable cap, made of an inexpensive, liquid impermeable material, such as plastic (e.g. PE, PP, nylon), soft plastic and silicone. In one embodiment, said cap has an inner surface coated with rubber or gelatin skin for further preventing leakage of liquids or gas.

The materials of the stoma cap and its accessories, as described above, are by no means limited to the specific materials listed herein, but include all suitable materials known to a person skilled in the art.

The objects of the present invention are also solved by a kit comprising a stoma coat as defined above, a circular flat washer as defined above (see, for example, FIG. 9), and, preferably, a collecting bag and a cap as defined above (see, for example, FIG. 10).

Preferably, said kit comprises a first circular flat washer and a second circular flat washer as defined above.

In one embodiment, said stoma coat as well as said first circular flat washer and said second circular flat washer are sterilized.

The objects of the present invention are also solved by a surgical method of making/creating a stoma in a body wall of the animal body, preferably of the human body, wherein said method comprises implanting the stoma coat as defined above into the animal body, preferably into the human body.

The stoma coat according to the present invention is applicable for temporary and permanent stomata. Preferably, said stoma is an end stoma.

In one embodiment, said implanting the stoma coat into the animal body, preferably into the human body, is performed by a procedure comprising the steps of:
a) reversing the flexible cone-shaped sleeve in order to expose the internal flange, wherein the wider end of the flexible cone-shaped sleeve is moved towards the distal end of the rigid tube (see, for example, FIG. 2);
b) bringing the internal flange in contact with the end of the body duct to be stomatized (see, for example, FIG. 3);
c) connecting the end of said body duct to the internal flange;
d) bringing the flexible cone-shaped sleeve back into its regular position (see, for example, FIGS. 1 and 4);
e) connecting the wider end of the flexible cone-shaped sleeve to the body duct;
f) inserting the rigid tube into an artificial opening (or tunnel) in a body wall, preferably the abdominal wall, of said animal body, preferably of said human body, so that the distal end of said rigid tube extends outside of said body wall and the distal surface of the external flange is in contact with the inner face of said body wall (see, for example, FIG. 4);
g) fixating the stoma coat, preferably by
screwing the first circular flat washer onto the rigid tube starting at the distal end of the rigid tube until the proximal surface of said first washer is in contact with the anterior fascia of the abdominal muscles (e.g. Musculus rectus abdominis) and connecting said first circular flat washer with the anterior fascia;

connecting said external flange with said inner face of said body wall, preferably with the peritoneum of the abdominal wall; and/or
screwing the second circular flat washer onto the rigid tube until the proximal surface of said second washer is in contact with the skin of said body wall, preferably the abdominal skin, after being closed and sutured around the head of the stoma coat.

Measures for preparing a patient for the above surgical procedure are known to the skilled person and include antibiotic prophylaxis and, if the colon is involved, medical and mechanical colon cleaning. Postoperative measures are also known to the skilled person. Preferably, after performance of the above surgical procedure, the patient is kept on a nothing-per-mouth (NPO) diet or on a clear liquids only diet for 5 to 7 days in order to allow for in-growth tissue into the mesh layer of those parts of the stoma coat coated therewith.

Techniques for preparing said end of the body duct to be stomatized and said artificial opening/tunnel in a body wall, preferably the abdominal wall, are known by the skilled person.

In one embodiment, said connecting the end of said body duct to the internal flange is performed by end-to-end anastomosis between said internal flange and the end of said body duct (e.g. the seromuscular layer with a small part of mucosa of a bowel end), wherein, preferably, said anastomosis is performed by multiple interrupted tension-free stitches using absorbable suture material.

In one embodiment, said connecting the wider end of the flexible cone-shaped sleeve to the body duct (e.g. the seromuscular layer of said body duct) is performed by suturing, preferably by multiple interrupted tension-free stitches using absorbable suture material.

In one embodiment, said screwing the first circular flat washer onto the rigid tube starting at the distal end of the rigid tube until the proximal surface of said first washer is in contact with the anterior fascia of the abdominal muscles, is accompanied by retraction of the skin and fat tissue of the abdominal wall in order to expose the anterior fascia. Preferably, said connecting said first circular flat washer with the anterior fascia is performed by suturing, preferably by transfixing interrupted tension-free stitches between the free edge of said first circular flat washer and the anterior fascia using non-absorbable suture material.

In one embodiment, said connecting said external flange with said inner face of said body wall, preferably with the peritoneum of the abdominal wall, is performed by suturing, preferably by transfixing interrupted tension-free stitches between the free edge of said external flange and said inner face of said body wall using absorbable suture material.

Preferably, closing and suturing of the abdominal skin is performed by approximating stitches around the head of the stoma coat using non-absorbable suture material.

Preferably, after implantation of the stoma coat, said head (region) of said rigid tube being located outside the body, i.e. outside the skin of the abdominal wall (extracutaneous or extraabdominal), has a length or is postoperationally adjusted (e.g. by using a saw) to a length of about 1 to 2 cm, preferably of about 1 to 1.5 cm. Preferably, a cap or collecting bag as defined above is applied to the head.

Particularly preferred indications for the use of a stoma coat according to the present invention are:
abdominal perineal resection (permanent colostomy—permanent stoma coat);
abdominal perineal resection with total colectomy (permanent ileostomy—permanent stoma coat);

any indication for the Hartman's procedure (temporary colostomy—temporary stoma coat); or any indication for temporary ureterostomy (temporary stoma coat).

The term "stoma coat", as used herein, is meant to refer to a prosthesis, more particularly to a prosthesis for implantation in a body/body wall for cooperating with a body duct to provide a stoma (or a highly controlled artificial fistula), i.e. a conduit for allowing elimination of waste material (e.g. feces or urine) from the patient's body. Preferably, said body duct is a bowel (e.g. the colon or ileum) or the ureter, wherein said body wall is the abdominal wall of a patient.

The term "cone-shape", as used herein (e.g., in "cone-shaped"), can also be referred to as a funnel-shape with a narrower and a wider opening at the two ends ("narrow end" and "wider end").

The term "rigid", as used herein, is meant to refer to a structure which is "not readily bendable by hand". However, it also refers to a structure which, even if it can be flexed by hand, is self-supporting and will not deflect perceptibly when held horizontally by one edge or margin (which may also referred to as "relatively rigid, but slightly flexible"). The term "flexible", as used herein, is meant to refer to a structure which is pliable by hand.

The terms "distal" and "proximal" as used herein refer to the position of the respective part of the stoma coat with respect to the animal, preferably human body, wherein "proximal" refers to a position closer to the center of the body, and "distal" refers to a position further away from the center of the body.

The term "anastomosis" refers to the connection of two structures, more specifically of two tubular structures, such as loops of intestine. For example, surgical anastomosis occurs when a segment of intestine is resected and the two remaining ends are sewn or stapled together (anastomosed). Another example is the connection between the end of the body duct to be stomatized and the internal flange of the stoma coat according to the present invention, thus providing a conduit for draining the content of said body duct via the rigid tube of the stoma coat.

The Hartmann's procedure is the surgical resection of the rectosigmoid colon with closure of the rectal stump and colostomy. It was initially used to treat colon cancer or diverticulitis. These days its use is limited to emergency surgery when immediate anastomosis is not possible, or more rarely it is used palliatively in colorectal tumours.

The present invention provides for an appliance, which allows to create a stoma, wherein the end of the body duct to be stomatized (e.g. the colon, ileum or ureter) stays inside the peritoneal cavity (intraperitoneal), at the level of the peritoneum. This is different to the traditional method of creating a stoma, wherein the opening of the body duct (bowel or ureter) is stitched to the skin of the abdomen, i.e. is located extracutaneous (extraabdominal).

The stoma coat according to the present invention prevents contact dermatitis and secondary infectious dermatitis, since there is no direct contact between the waste material (e.g. bowel contents or urine) and the skin. Furthermore, no adhesive materials, which may cause allergic reactions of the skin, are used.

Because the stomatized body duct is not exposed to the air and fixated in a relatively relaxed state, i.e. without much tension (which tension may, for example, compromise blood supply), the stoma coat also prevents ischemic necrosis, strangulation, retraction of the body duct (e.g. stomal bowel retraction), stenosis or obstruction. Furthermore, the structure of the stoma coat prevents friction with the mucosa, thus lowering the risk of ischemic mucosal damage and other complications such as bowel dysplasia or carcinoma, which are observed when appliances are frequently inserted and removed into/from the foramen of a preexisting stoma.

The cone-shape of the flexible sleeve or body of the stoma coat, which basically functions as a body duct (e.g. bowel) container, prevents an undesirable compression of the body duct, and thus lowers the risk of stomal voiding dysfunction. It also makes the sleeve more adjustable to a wide range of body duct diameters. Together with the external flange, the flexible cone-shaped sleeve further prevents sliding of the stoma coat as well as peristomal herniation in the abdominal wall. Furthermore, the cone-shape facilitates reversing the flexible sleeve in order to allow for anastomosis between the end of the body duct and the internal flange. The cone-shape of the sleeve and the external flange further prevent prolapse of the colon or ileum.

The rigid head of the stoma coat protruding from the skin of the patient may be further modified, for example by adding a filling sensor, which indicates when to apply the collecting bag.

The stoma coat according to the present invention is suitable for patients of all age groups. It is mainly designed for colostomy and ileostomy, but is also applicable in urostomy (ureterostomy). The stoma coat is comfortable for the patient, but at the same time reliable and secure. For example, the multiple levels of fixation of the stoma coat (skin, fascia, peritoneum, body duct) protect it from a sudden increase in intra-abdominal pressure, e.g. due to coughing or sneezing or during sports activities. Its cleaning and maintenance is easy and time saving. The accessorial collecting bag and cap can be easily applied by the patient himself/herself. Last but not least, the manufacture of the stoma coat according to the present invention is relatively inexpensive.

Reference is made to the figures, wherein

Figure 1:
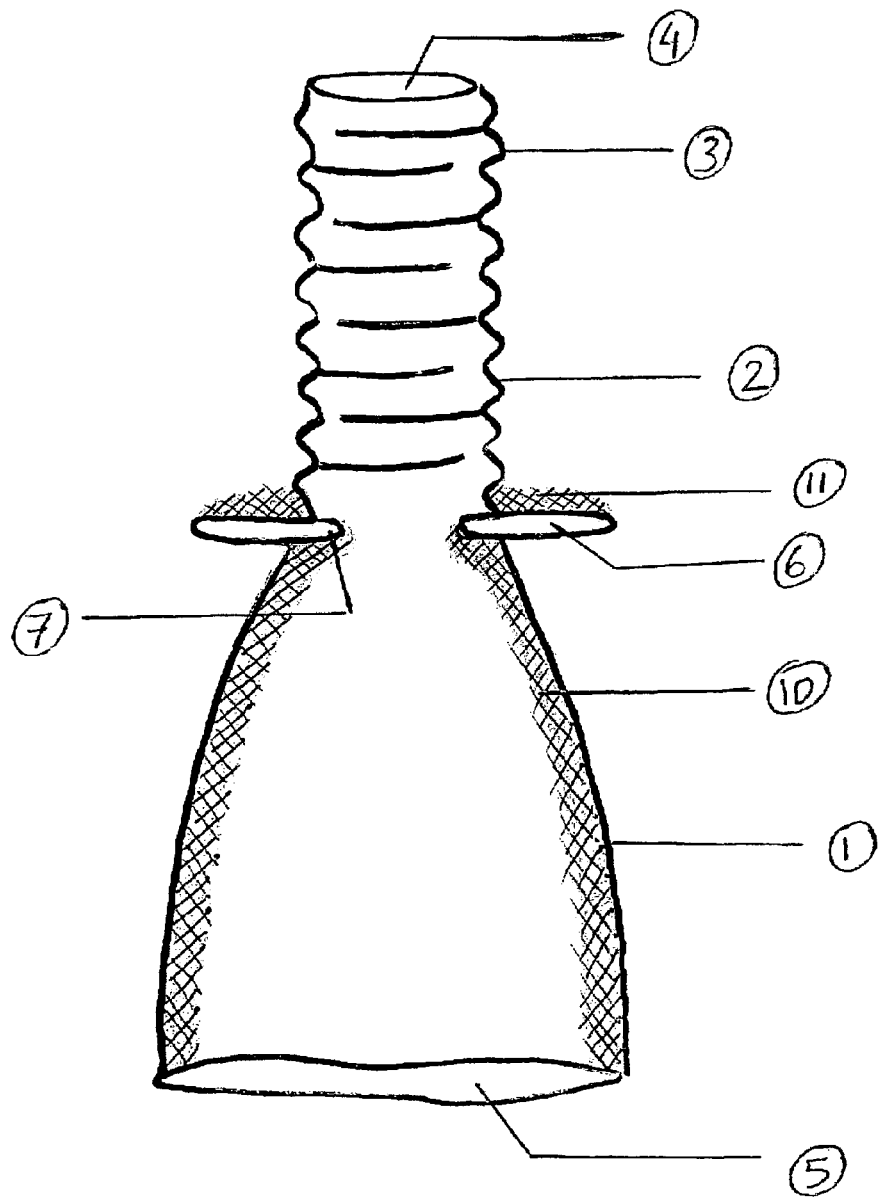
FIG. 1 is a schematic view of the stoma coat according to the present invention before surgical implantation, with the flexible cone-shaped sleeve being in its regular position.
Figure 2:
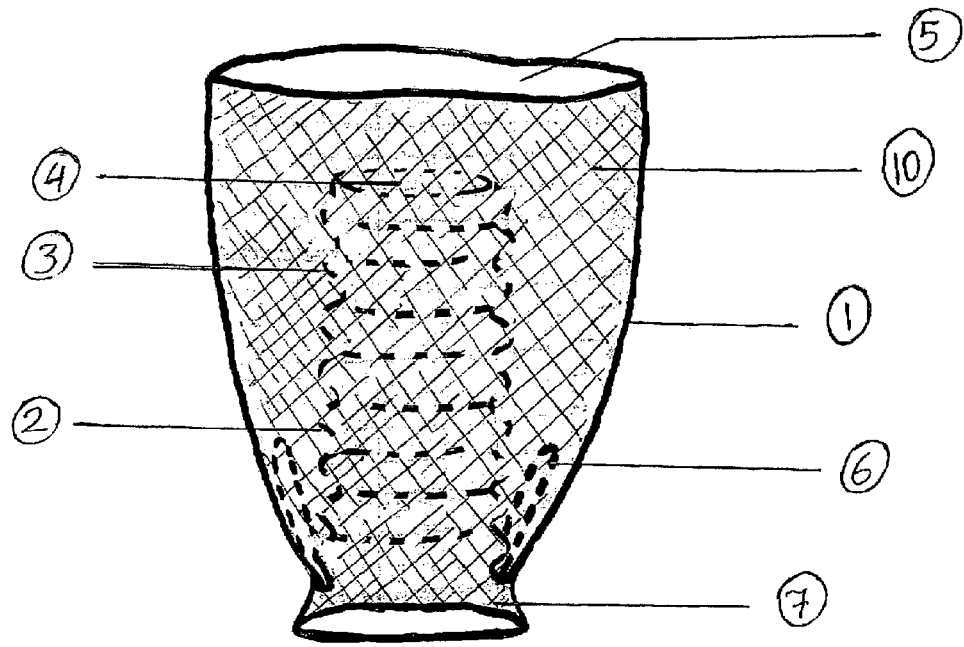
FIG. 2 is a schematic view of the stoma coat according to the present invention before surgical implantation, with the flexible cone-shaped sleeve being in its reversed position.
Figure 3:
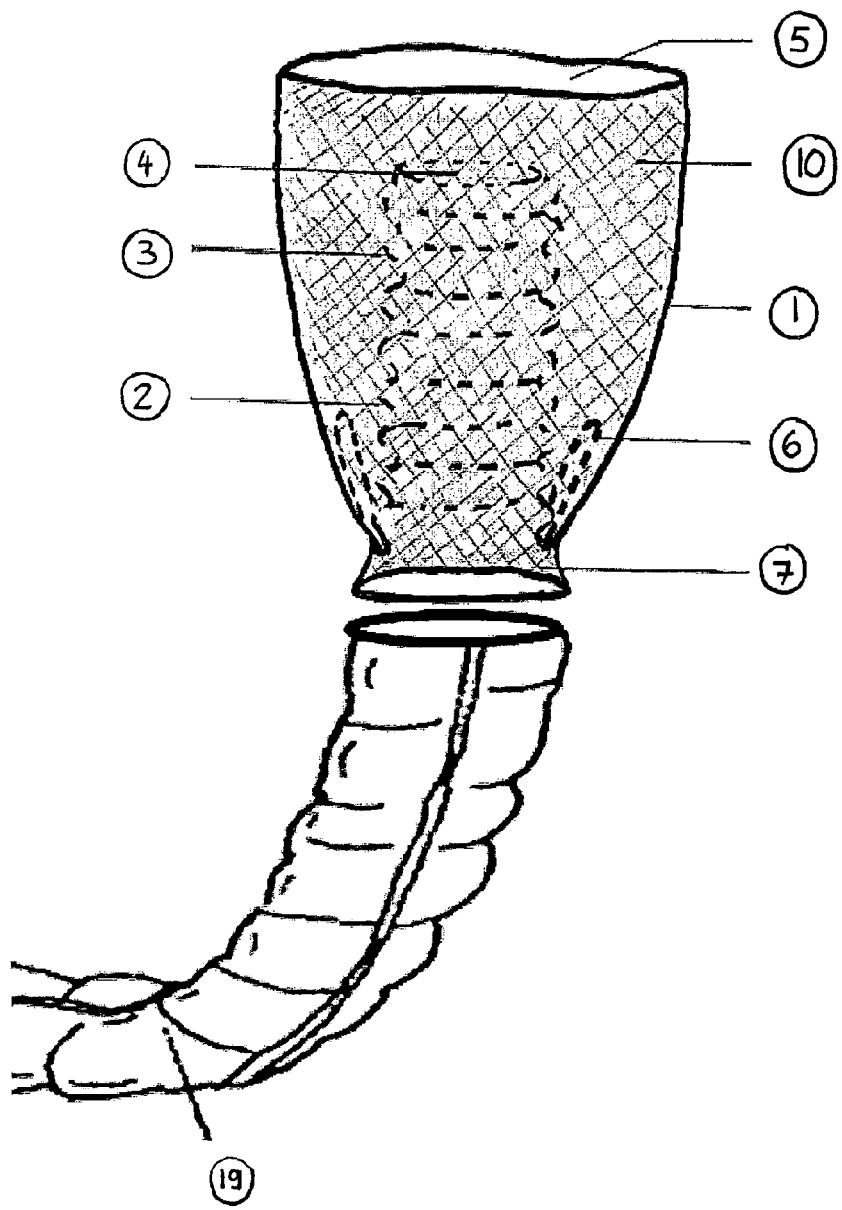
FIG. 3 is a schematic view of the stoma coat according to the present invention, with the flexible cone-shaped sleeve being in its reversed position, and the internal flange being aligned with the artificial bowel end.
Figure 4:
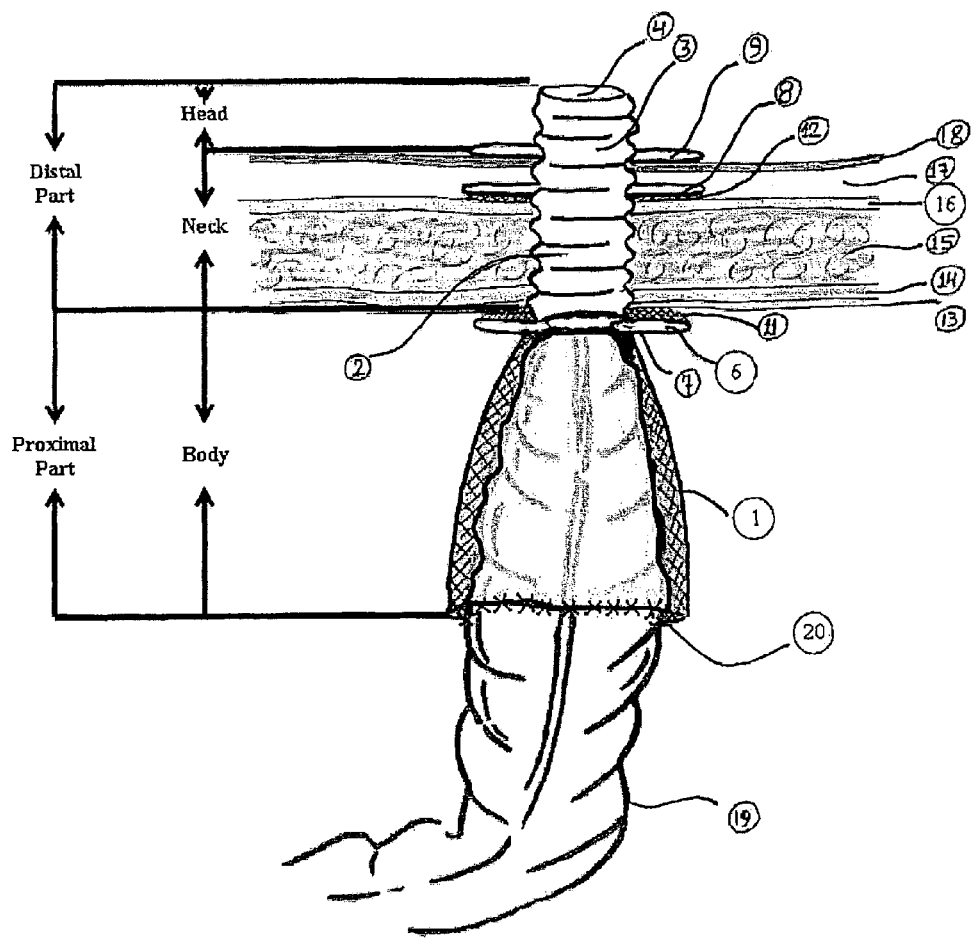
FIG. 4 is a schematic view of the stoma coat according to the present invention after surgical implantation into the abdominal wall and abdominal cavity.
Figure 5:
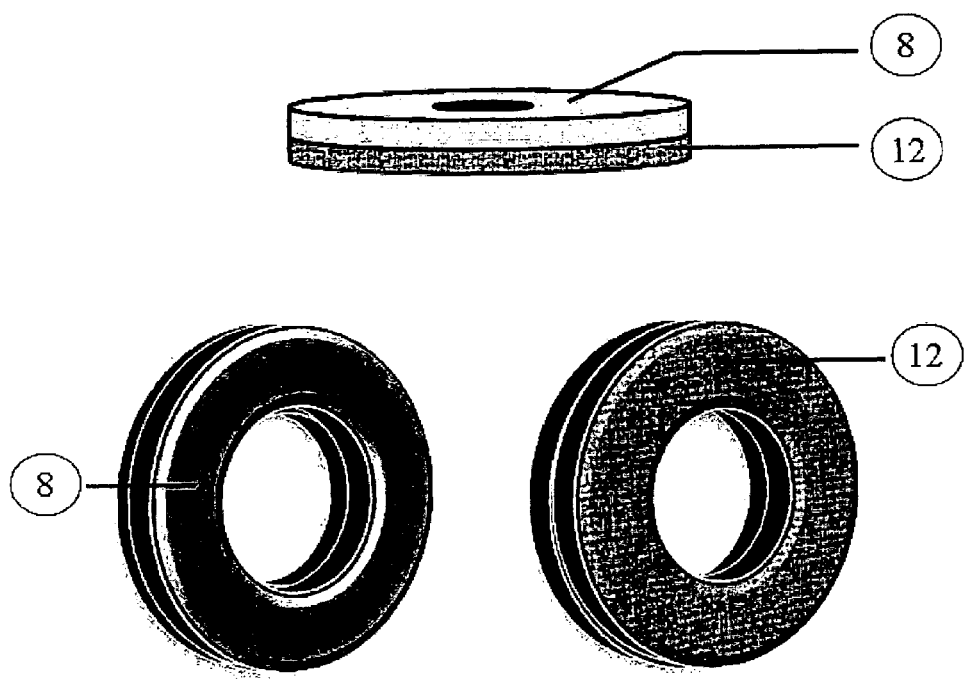
FIG. 5 is a schematic view of the first circular flat washer (fascia washer), wherein one side of said circular flat washer is coated with a mesh promoting in-growth of animal tissue, preferably human tissue.
Figure 6:
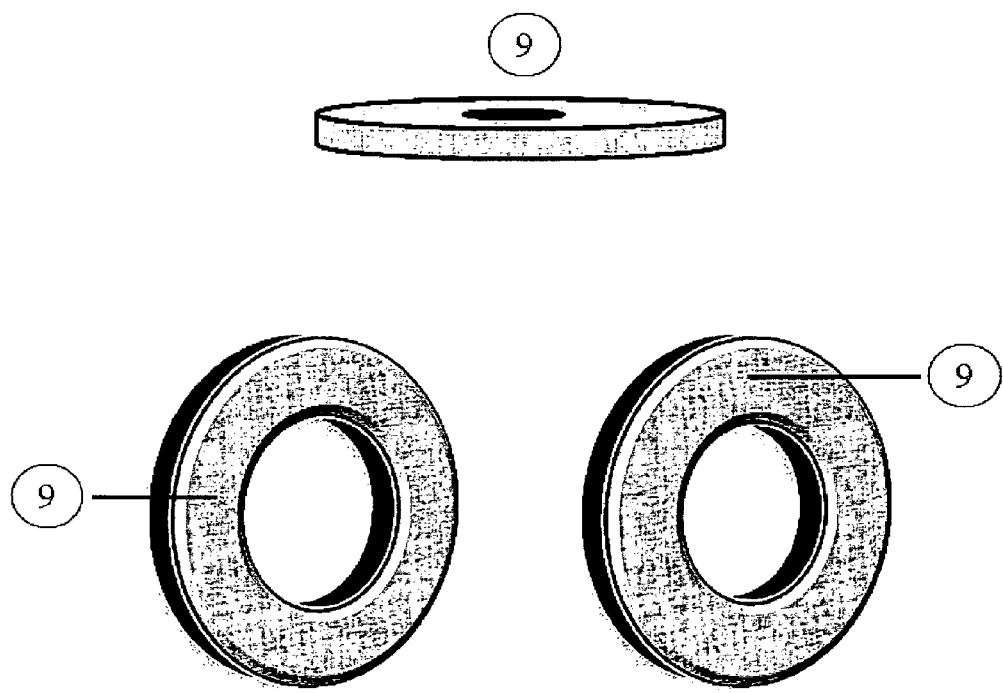
FIG. 6 is a schematic view of the second circular flat washer (skin washer) with both sides of the washer having a smooth surface.
Figure 7:
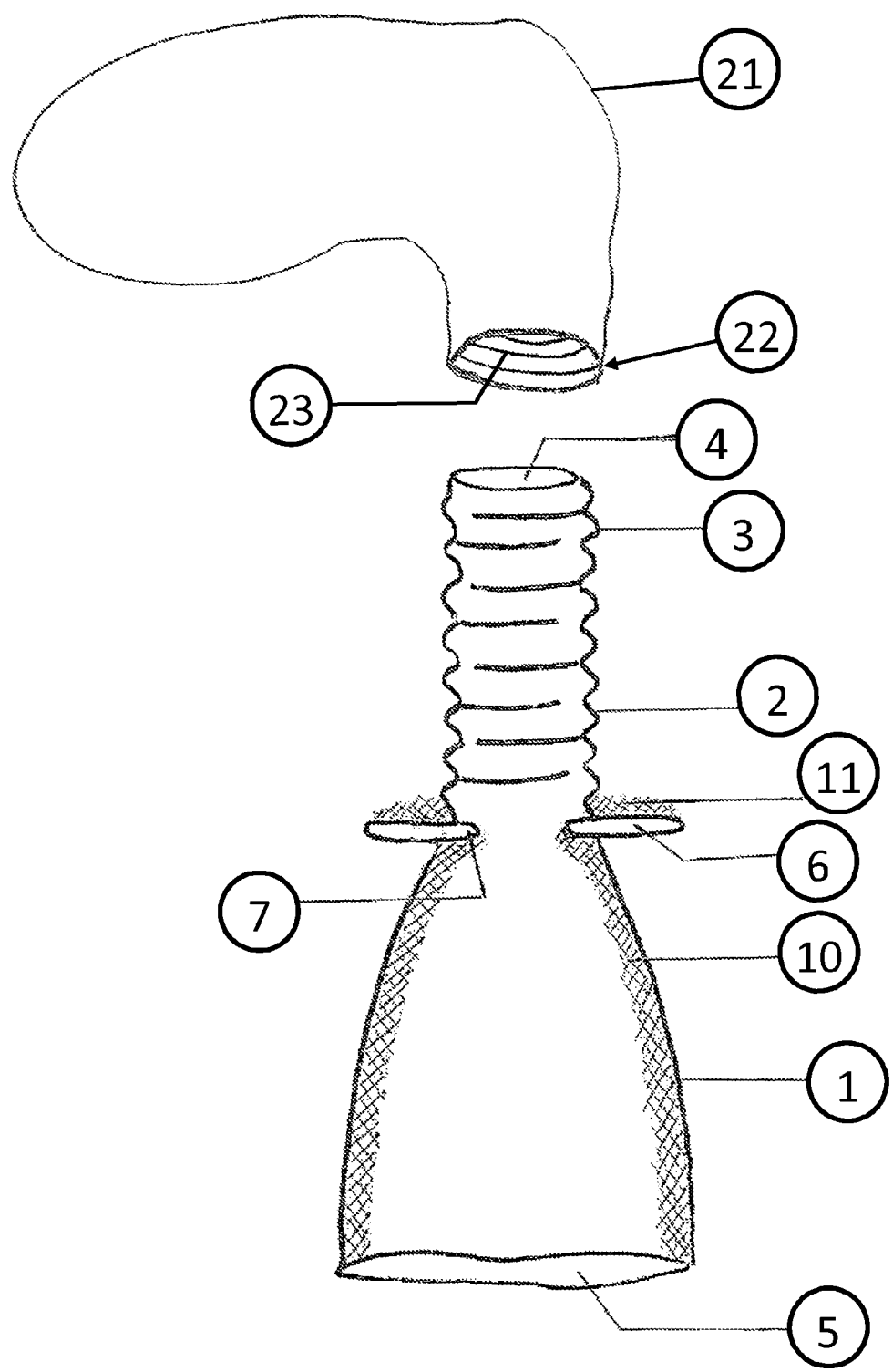
FIG. 7 is a schematic view of a collecting bag for use with the stoma coat according to the present invention.
Figure 8:
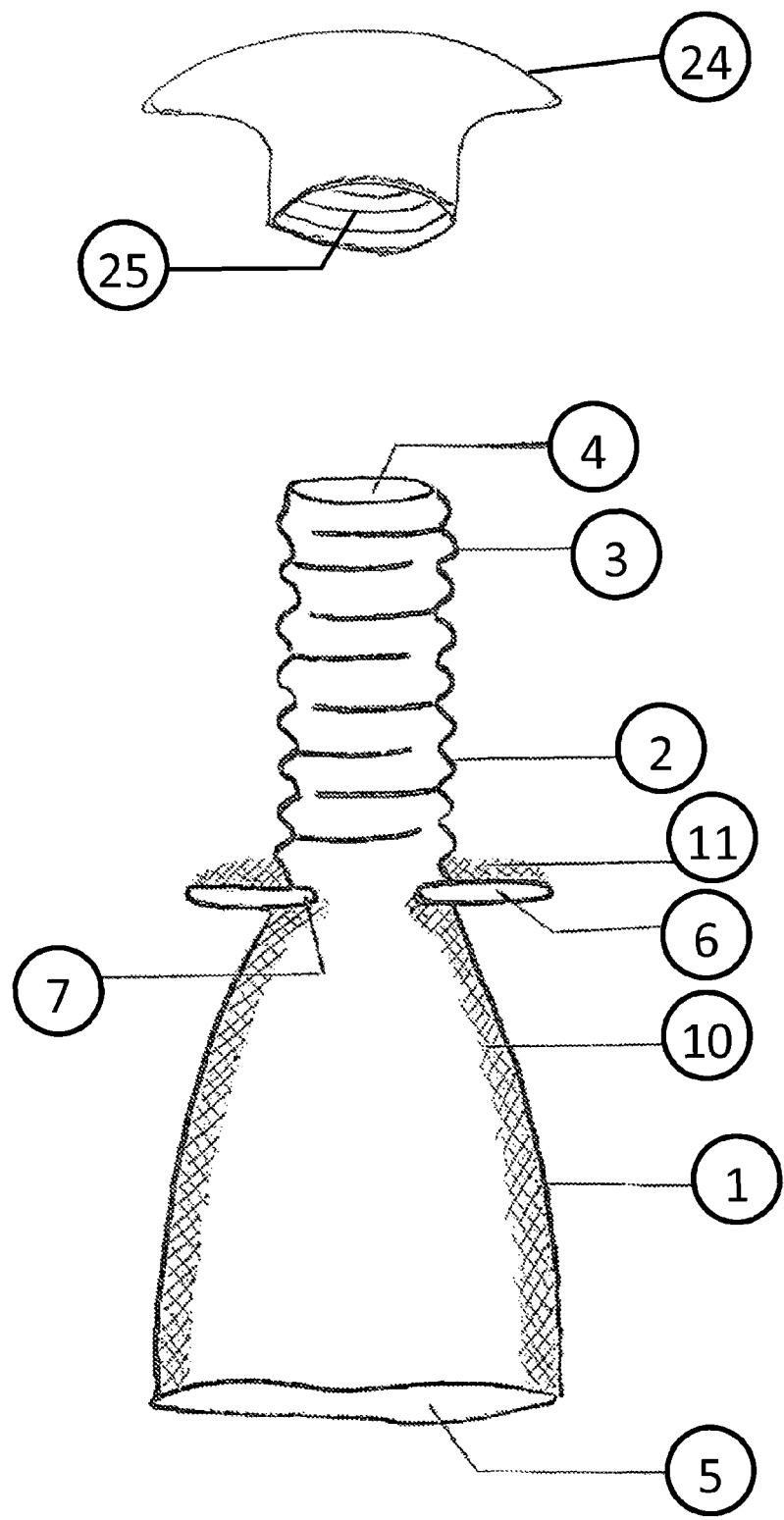
FIG. 8 is a schematic view of a cap for use with the stoma coat according to the present invention.
Figure 9:
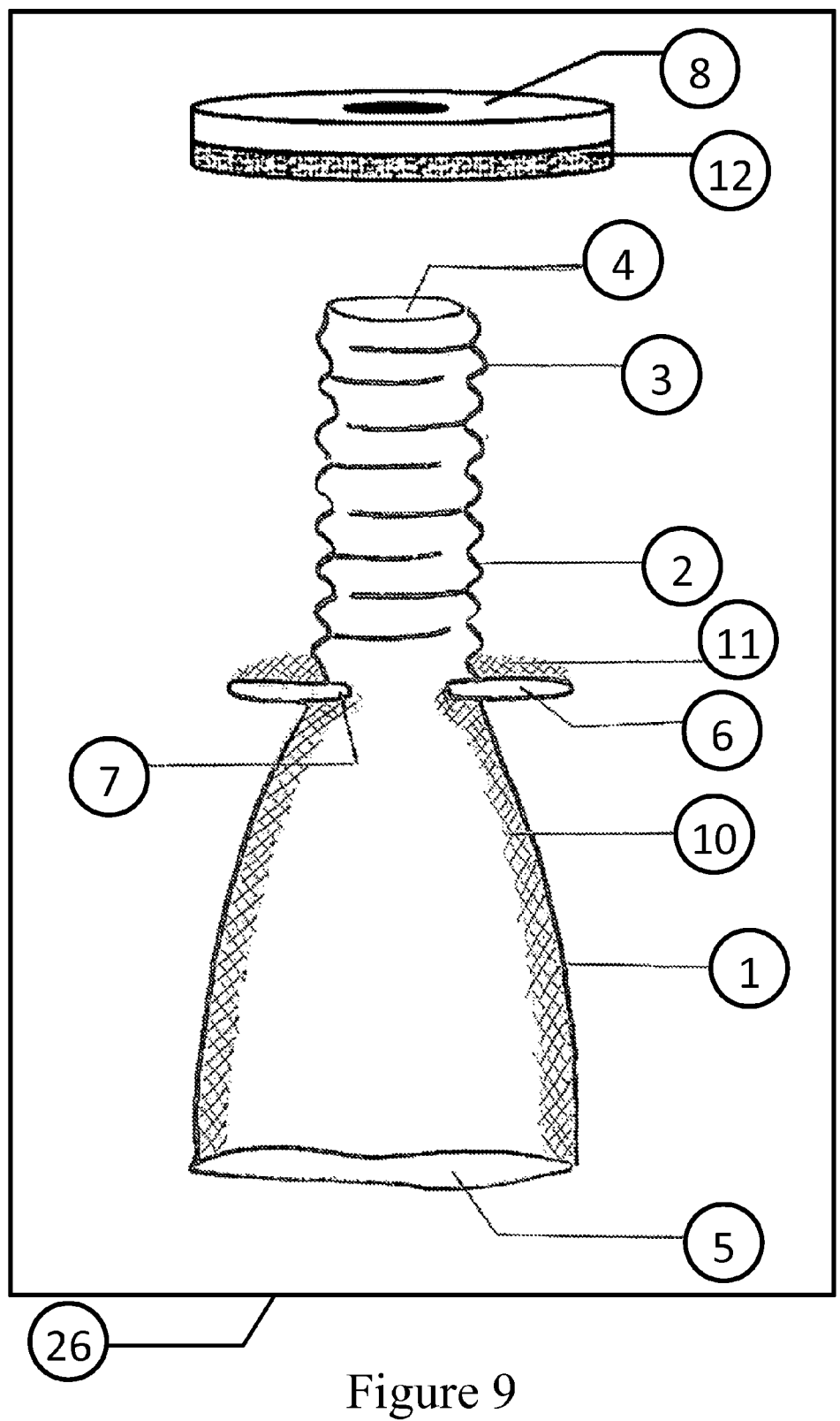
FIG. 9 is a schematic view of a kit comprising a stoma coat and a flat circular washer in accordance with the present invention.
Figure 10:
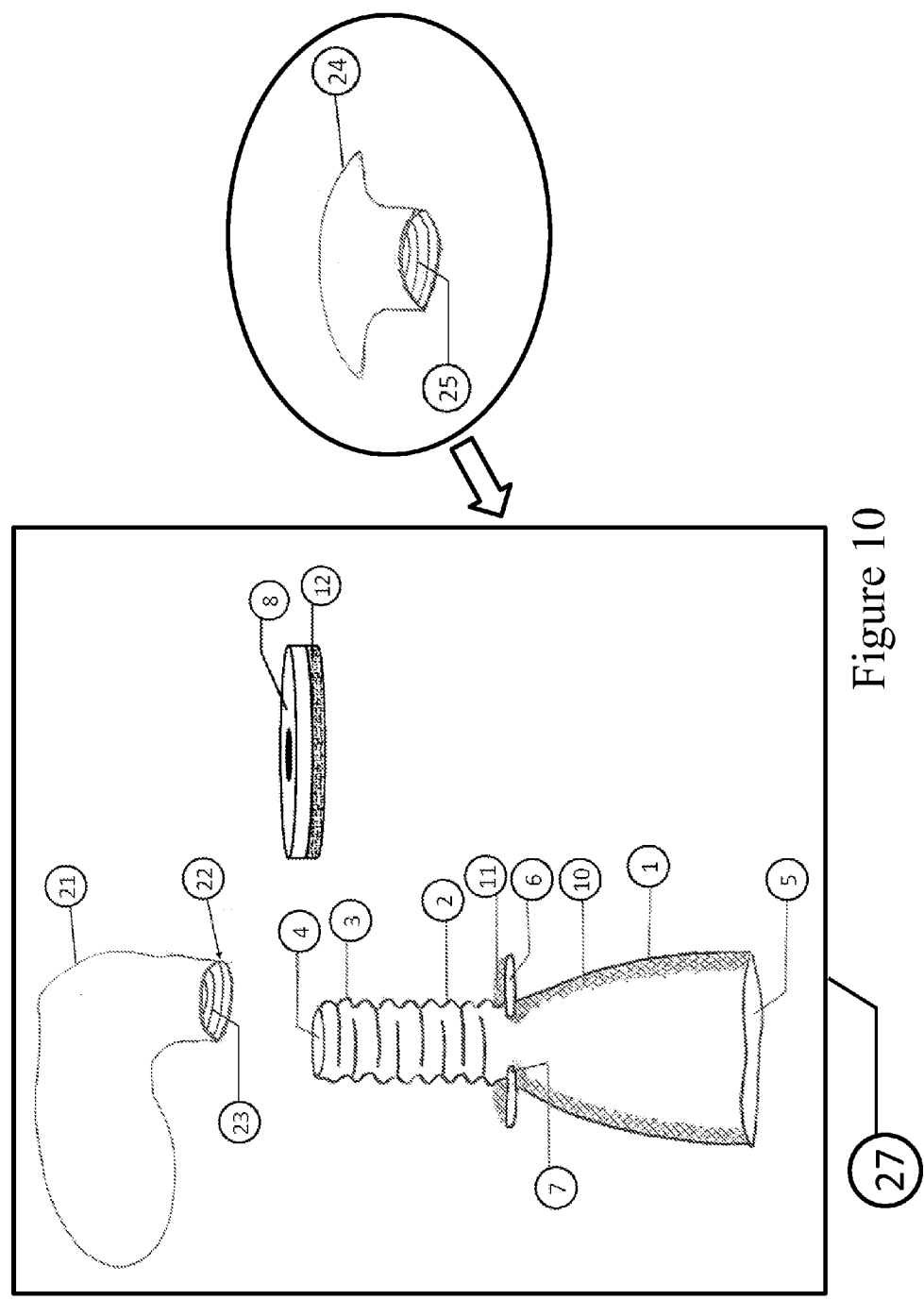
FIG. 10 is a schematic view of a kit comprising a stoma coat, circular washer, collecting bag and optionally a cap in accordance with the present invention.

The reference numerals used in the above figures refer to (preferred embodiments of) the following features:

(1) flexible cone-shaped sleeve (also referred to as body of the stoma coat)
(2) rigid tube (neck)
(3) rigid tube (head)
(4) distal opening of the stoma coat at the distal end of the rigid tube
(5) proximal opening of the stoma coat at the wider end of the flexible cone-shaped sleeve
(6) external flange
(7) internal flange
(8) first circular flat washer (fascia washer)
(9) second circular flat washer (skin washer)
(10) mesh layer on the inner surface of the flexible cone-shaped sleeve
(11) mesh layer on the distal surface of the external flange
(12) mesh layer on the proximal surface of the first circular flat washer (fascia washer)
(13) peritoneum
(14) posterior fascia
(15) abdominal muscles (e.g. Musculus rectus abdominis)
(16) anterior fascia
(17) fat tissue
(18) abdominal skin
(19) bowel
(20) anastomosis between the wider end of the flexible cone-shaped sleeve and the bowel
(21) collecting bag
(22) opening of the collecting bag
(23) threaded linking piece of the collecting bag
(24) cap
(25) threaded portion of the cap
(26) kit including stoma coat and first circular washer
(27) kit including stoma coat, first circular washer and collecting bag, optionally including a cap

The invention claimed is:

1. A stoma coat, comprising:
a flexible cone-shaped sleeve of a first biocompatible material having a narrow end and a wider end opposite of said narrow end, and further having an external flange comprising a distal surface and an internal flange located at said narrow end, wherein the distal surface of the external flange is configured to be in contact with an inner surface of a body wall of an animal body; and
a rigid tube of a second biocompatible material having an outside diameter, a distal end and a proximal end opposite of said distal end, and further having a smooth inner surface and a threaded outer surface, wherein said proximal end is connected with said narrow end of said cone-shaped flexible sleeve.

2. The stoma coat according to claim 1, wherein said external flange and said internal flange are made of said first biocompatible material.

3. The stoma coat according to claim 1, wherein said first biocompatible material is selected from the group consisting of plastics and silicones.

4. The stoma coat according to claim 1, wherein said second biocompatible material is a polyolefin.

5. The stoma coat according to claim 1, wherein said flexible cone-shaped sleeve has an inner surface and an outer surface, wherein only said inner surface is coated with a mesh promoting in-growth of animal tissue.

6. The stoma coat according to claim 1, wherein said external flange has a distal surface and a proximal surface, wherein only said distal surface is coated with a mesh promoting in-growth of animal tissue.

7. The stoma coat according to claim 1, further comprising a first circular flat washer having a circular opening with a diameter matching said outside diameter of said rigid tube, wherein said first circular flat washer is a threaded washer and is screwed onto said rigid tube.

8. The stoma coat according to claim 7, wherein said first circular flat washer has a distal surface and a proximal surface, wherein only said proximal surface is coated with a mesh promoting in-growth of animal tissue.

9. The stoma coat according to claim 7, further comprising a second circular flat washer having a circular opening with a diameter matching said outside diameter of said rigid tube, wherein said second circular flat washer is a threaded washer and is screwed onto said rigid tube, wherein said second circular flat washer is closer to said distal end of said rigid tube than said first circular flat washer.

10. A method for making a stoma in a body wall of an animal body, wherein said method comprises implanting a stoma coat according to claim 1 in the body wall of the animal body, wherein the animal body comprises a body duct and the stoma coat cooperates with the body duct to provide a stoma.

11. The stoma coat according to claim 1, further comprising a collecting bag, wherein said collecting bag comprises an opening with a circular threaded linking piece having an inside diameter matching said outside diameter of said rigid tube of said stoma coat, and wherein said collecting bag is removably screwed onto said distal end of said rigid tube.

12. The stoma coat according to claim 1, further comprising a cap, wherein said cap is a threaded cap having an inside diameter matching said outside diameter of said rigid tube of said stoma coat, and wherein said cap is removably screwed onto said distal end of said rigid tube.

13. A kit comprising a stoma coat according to claim 1 wherein said stoma coat comprises a rigid tube with an outside diameter, wherein said kit further comprises a circular flat washer wherein said circular flat washer is a threaded washer having a circular opening with a diameter matching the outside diameter of the rigid tube of the stoma coat.

14. The kit according to claim 13, further comprising a collecting bag for use with the stoma coat, wherein said collecting bag comprises an opening with a circular threaded linking piece having an inside diameter matching the outside diameter of the rigid tube of the stoma coat, and wherein said collecting bag can be screwed onto the distal end of the rigid tube, and wherein said kit further optionally comprises a cap for use with the stoma coat, wherein said cap is a threaded cap having an inside diameter matching the outside diameter of the rigid tube of the stoma coat, and wherein said cap can be screwed onto the distal end of the rigid tube.

15. The stoma coat according to claim 3, wherein said first biocompatible material is silicone rubber.

16. The stoma coat according to claim 4, wherein said second biocompatible material is selected from the group consisting of polypropylene, polyethylene, and copolymers thereof.

17. The stoma coat according to claim 1, wherein said stoma coat comprises a distal part and a proximal part, and wherein the rigid tube has a cylindrical shape that forms the distal part of the stoma coat and said flexible cone-shaped sleeve forms the proximal part of said stoma coat.

18. The stoma coat according to claim 1, wherein said internal flange and said external flange are aligned.

19. The stoma coat according to claim 1, wherein said flexible cone-shaped sleeve has a length of about 8 to 15 cm.

20. The stoma coat according to claim 1, wherein said rigid tube has a length of about 5 to 15 cm.

21. The stoma coat according to claim 6, wherein said mesh is a biocompatible non-absorbable material selected from the group consisting of: polypropylene (PP) and expanded polytetrafluorethylene (e-PTFE).

22. The stoma coat according to claim 1, wherein the internal flange is coated with a mesh promoting in-growth of animal tissue.

23. The stoma coat according to claim 1, wherein the external flange protrudes about 2 to 5 cm from said flexible cone-shaped sleeve and/or the internal flange protrudes about 0.5 to 1.5 cm from said flexible cone-shaped sleeve.

24. The stoma coat according to claim 11, wherein the rigid tube further comprises a filling sensor to detect when to apply the collecting bag.

25. The stoma coat according to claim 7, wherein the first circular flat washer is made of a biocompatible, non-absorbable material selected from the group consisting of: nylon, polypropylene and prolene.

26. The stoma coat according to claim 7, wherein the first circular flat washer protrudes about 2.5 to 3.5 cm from said rigid tube when screwed onto said rigid tube.

27. The stoma coat according to claim 9, wherein the second circular flat washer is made of a biocompatible, non-absorbable material selected from the group consisting of: nylon, polypropylene and prolene.

28. The stoma coat according to claim 9, wherein the second circular flat washer protrudes about 3 to 5 cm from said rigid tube when screwed onto said rigid tube.

29. The stoma coat according to claim 11, wherein the collecting bag is made of a liquid impermeable material selected from the group consisting of: plastic, rubber and silicone.

30. The stoma coat according to claim 12, wherein the cap is made of a liquid impermeable material selected from the group consisting of: plastic, rubber and silicone.

31. The stoma coat according to claim 12, wherein the cap has an inner surface coated with rubber or gelatin.

32. The method according to claim 10, wherein the body duct is the peritoneal cavity and the body wall is the abdominal wall.

* * * * *